United States Patent
Breipohl et al.

(10) Patent No.: US 6,437,136 B2
(45) Date of Patent: *Aug. 20, 2002

(54) PROCESS FOR THE PREPARATION OF (−) CIS-3-HYDROXY-1-METHYL-4-(2,4,6-TRIMETHOXYPHENYL)PIPERIDINE

(75) Inventors: Gerhard Breipohl, Frankfurt; Jürgen Michalowsky, Kelkheim, both of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/842,832

(22) Filed: Apr. 27, 2001

Related U.S. Application Data

(63) Continuation of application No. 09/600,775, filed as application No. PCT/EP98/08327 on Dec. 18, 1998, now Pat. No. 6,225,473.

(30) Foreign Application Priority Data

Jan. 23, 1998 (DE) .......................................... 198 02 449

(51) Int. Cl.⁷ ..................... C07D 211/02; C07D 211/44; C07D 401/00
(52) U.S. Cl. .......................... 546/185; 546/196; 546/217
(58) Field of Search ................................. 546/185, 196, 546/217

(56) References Cited

U.S. PATENT DOCUMENTS 6,225,473 B1 * 5/2001 Breipohl et al. ............ 546/185

* cited by examiner

*Primary Examiner*—Alan L. Rotman
*Assistant Examiner*—Raymond Covington
(74) *Attorney, Agent, or Firm*—Finnegan, Henderson, Farabow, Garrett & Dunner, LLP

(57) ABSTRACT

Disclosed is a method for producing (−)cis-3-hydroxy-1-methyl-4-(2,4,6-trimethoxyphenyl)-piperidine characterized in that 1-methyl-piperidine-4-one is converted into hydrobromide, subsequently transformed with bromine into 3(R,S)-bromine-1-methyl-4-oxo-piperidine-hydrobromide and reacted with 1,3,5-trimethoxybenzol to form 3(R,S)-bromine-1-methyl-4-(2,4,6-trimethoxyphenyl)-1,2,3,6-tetrahydro-pyridine-hydrobromide. By stirring the reaction solution into an organic solvent, 3(R,S)-bromine-1-methyl-4-(2,4,6-trimethoxyphenyl)-1,2,3,6-tetrahydro-pyridine-hydrobromide is initially isolated as a solid and subsequently the product is mixed with water and converted into 3(R,S)-hydroxy-1-methyl-4-(2,4,6-trimethoxyphenyl)-1,2,3,6-tetrahydro-pyridine by means of stirring. The product thus prepared is catalytically hydrogenated into a racemic 3,4-cis-alcohol and subsequently, enantiomerically pure (−)cis-3-hydroxy-1-methyl-4-(2,4,6-trimethoxyphenyl)-piperidine is obtained by separation of racemic mixtures with chiral auxiliary reagents from racemic 3,4-cis alcohol.

31 Claims, No Drawings

PROCESS FOR THE PREPARATION OF (−) CIS-3-HYDROXY-1-METHYL-4-(2,4,6-TRIMETHOXYPHENYL)PIPERIDINE

This is a continuation of application Ser. No. 09/600,775, filed Jul. 21, 2000, now U.S. Pat. No. 6,225,473, which is a 371 of PCT/EP98/08327, filed Dec. 18,1998, both of which are incorporated herein by reference.

(−)cis-3-Hydroxy-1-methyl-4-(2,4,6-trimethoxyphenyl) piperidine (II) is a central building block in the synthesis of flavopiridol (I) (HMR 1275 or L86-8275), the first potent inhibitor of the cyclin-dependent protein kinase (see, for example, Sedlacek, Hans Harald; Czech, Joerg; Naik, Ramachandra; Kaur, Gurmeet; Worland, Peter; Losiewicz, Michael; Parker, Bernard; Carlson, Bradley; Smith, Adaline; et al. Flavopiridol (L86 8275; NSC 649890), a new kinase inhibitor for tumor therapy. Int. J. Oncol. (1996), 9(6), 1143–1168 or Czech, Joerg; Hoffmann, Dieter; Naik, Ramachandra; Sedlacek, Hans-Harald. Antitumoral activity of flavone L 86-8275. Int. J. Oncol. (1995), 6(1), 31–36).

The process for the preparation of (II) previously described in EP-B 0 241 003 and EP-B 0 366 061 is time-consuming and includes reactions (hydroboration, Swern oxidation, sodium borohydride reduction) which are difficult to handle on the industrial scale. Surprisingly, we have now found a significantly simpler preparation process, which is illustrated in Scheme 1.

Scheme 1:

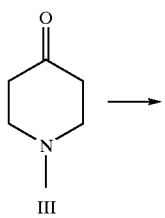
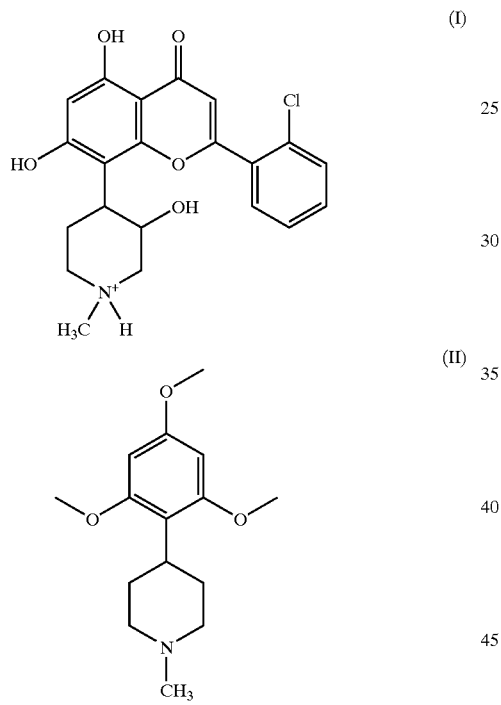
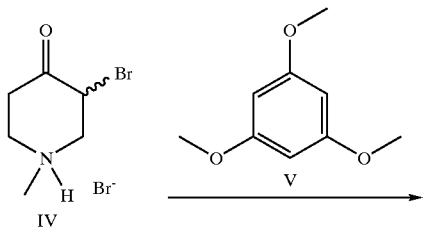
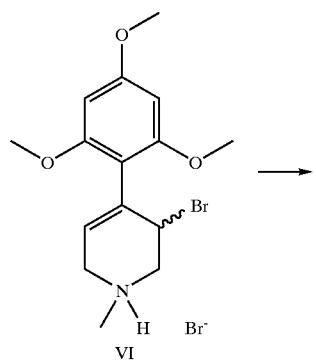
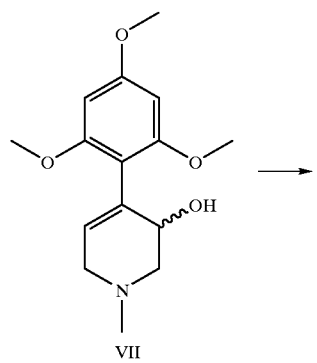

The process for the preparation of (−)cis-3-hydroxy-1-methyl-4-(2,4,6-trimethoxyphenyl)piperidine (II)

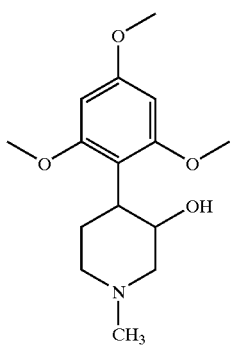

(II)

comprises a$_1$) converting 1-methylpiperidin-4-one (III)

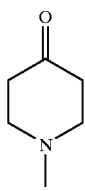

III into the hydrobromide according to known processes, or a$_2$) converting 1-methylpiperidin-4-one (III) directly into the hydrobromide, prior to the subsequent bromination, by introduction of 1-methylpiperidin-4-one into an HBr/glacial acetic acid solution, and b) reacting 1-methylpiperidin-4-one hydrobromide in a suitable solvent, acetic acid, in the temperature range from 0° C.–30° C. with bromine to give 3(R,S)-bromo-1-methyl-4-oxopiperidine hydrobromide (IV)

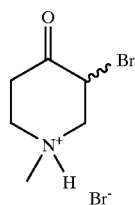

IV c) reacting this intermediate (IV) directly by addition of 0.8–1 equivalent of 1,3,5-trimethoxybenzene (V)

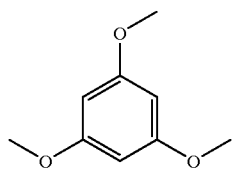

V to the reaction solution at 0–30° C. to give 3(R,S)-bromo-1-methyl-4-(2,4,6-trimethoxyphenyl)-1,2,3,6-tetrahydropyridine hydrobromide (VI)

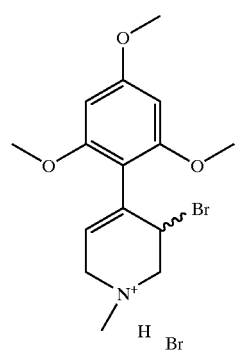

VI and, if appropriate, additionally adding acetic anhydride to remove any water of reaction formed d$_1$) first isolating the compound (VI) as a solid by stirring the reaction solution into a suitable organic solvent, methyl tert-butyl ether, dichloromethane etc., and subsequently reacting the resulting product with water and by stirring at 50°–100° C., preferably at 60°–80° C., to give 3(R,S)-hydroxy-1-methyl-4-(2,4,6-trimethoxyphenyl)-1,2,3,6-tetrahydropyridine (VII)

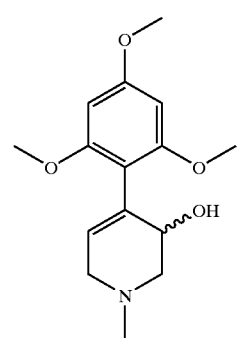

VII or d$_2$) treating the reaction mixture containing the compound (VI) directly with water and reacting by stirring at 50°–100° C., preferably at 60°–80° C., to give 3(R,S)-hydroxy-1-methyl-4-(2,4,6-trimethoxyphenyl)-1,2,3,6-tetrahydropyridine (VII), and d$_3$) cooling the reaction mixtures obtained according to d$_1$) or d$_2$), if appropriate diluting further with water and adjusting to pH>12 at 0°–30° C. by addition of aqueous alkali, preferably sodium hydroxide, 3(R,S)-hydroxy-1-methyl-4-(2,4,6-trimethoxyphenyl)-1,2,3,6-tetrahydropyridine (VII) precipitating, filtering off the resulting crude product with suction and if appropriate, for purification, taking it up again in aqueous hydrochloric acid, filtering and optionally extracting with a water-immiscible solvent, e.g. ethyl acetate, and then adjusting the aqueous phase to pH>12 by addition of aqueous alkali, preferably sodium hydroxide, 3(R,S)-hydroxy-1-methyl-4-(2,4,6-trimethoxyphenyl)-1,2,3,6-tetrahydropyridine (VII) precipitating, extracting the precipitated product, if appropriate for further purification, with one or more suitable organic solvents, acetone, isopropanol, diisopropyl ether or alternatively mixtures of these solvents, and e$_1$) catalytically hydrogenating the resulting product (VII) in a suitable solvent, e.g. methanol, isopropanol, water or mixtures of these solvents using a suitable catalyst, e.g. palladium/carbon, rhodium/carbon etc., to give the racemic 3,4-cis alcohol (VIII)

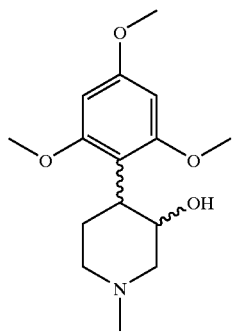

VIII where the 3,4-trans alcohol, which possibly results in small amounts during the reduction, can be removed by crystallization from suitable solvents, acetone, or e2) for the hydrogenation, employing easily accessible esters (IXa) or carbonates (IXb) of the compound (VII)

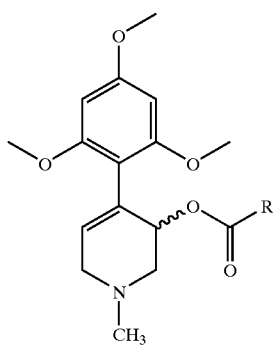

IXa

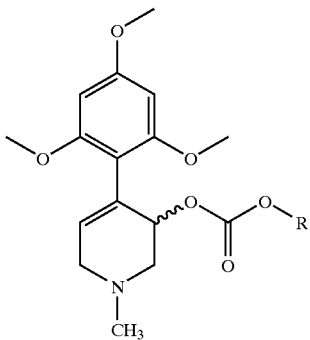

IXb in which R is $(C_1-C_{16})$-alkyl, $(C_6-C_{14})$-aryl-$(C_1-C_{16})$-alkyl or $(C_6-C_{14})$-aryl and in the formula (IXa) is further carboxy-$(C_2-C_6)$-alkyl;

compounds (Xa) and (Xb) being obtained, from which the compound (VIII) can be liberated by known procedures, f₁) obtaining the enantiomerically pure cis alcohol (II) from the compound (VIII) by a known process by resolution using suitable chiral auxiliary reagents such as, for example, ketopinic acid, or f₂) carrying out the resolution using the compounds (Xa) or (Xb)

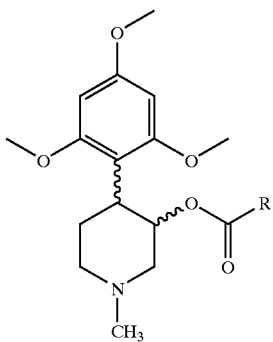

Xa

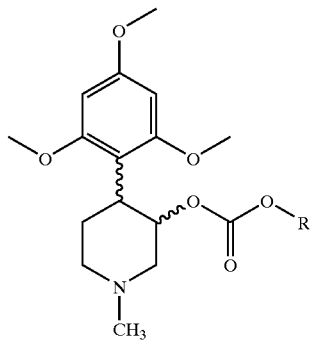

Xb where R is $(C_1-C_{16})$-alkyl, $(C_6-C_{14})$-aryl-$(C_1-C_{16})$-alkyl or $(C_6-C_{14})$-aryl and in the formula (Xa) is further carboxy-$(C_2-C_6)$-alkyl, and then converting these into the compound (II) by known processes, it also being possible to exchange the sequence of the reaction steps e) and f, i.e. also to carry out the resolution as early as at the stage of the allyl alcohol (VII) or of the compounds (IXa) and (IXb) obtained therefrom.

In analogy to a process described in the literature (Trost et al., JACS 1994, 116, 10320), the esters (IXa) or carbonates (IXb) are suitable for the deracemization to give the enantiomerically pure esters. After hydrogenation and ester cleavage, (−)cis-3-hydroxy-1-methyl-4-(2,4,6-trimethoxyphenyl)piperidine (II) is then obtained.

3(R,S)-Bromo-1-methyl-4-(2,4,6-trimethoxyphenyl)-1,2,3,6-tetrahydropyridine hydrobromide (VI) and 3(R,S)-hydroxy-1-methyl-4-(2,4,6-trimethoxyphenyl)-1,2,3,6-tetrahydropyridine (VII) are valuable intermediates in the preparation of (−)cis-3-hydroxy-1-methyl-4(2,4,6-trimethoxyphenyl)piperidine (II).

EXAMPLES

Example 1

Preparation of 3(R,S)-Bromo-1methyl-4-(2,4,6-trimethoxyphenyl)-1,2,3,6-tetrahydropyridine Hydrobromide (VI)

75.7 ml (0.44 mol) of 33% strength HBr in glacial acetic acid were added to 200 ml of glacial acetic acid, and 50 g (0.44 mol) of 1-methylpiperidin-4-one (III) were then rapidly added dropwise at 20–25° C. with ice-cooling. 70.4 g (0.44 mol) of bromine were added dropwise at 20–25° C. in the course of 30 min to the suspension of the hydrobromide obtained in this way, a clear, yellowish solution being obtained. This was stirred at 25° C. for a further 15 min and 67.2 g (0.40 mol) of 1,3,5-trimethoxybenzene (V) were then added to the reaction solution. It was then stirred at 25° C. for 1 h. After this, 300 ml of methyl tert-butyl ether were allowed to run in, the product being deposited in oily form. The supernatant was decanted off, the residue was stirred again with 300 ml of methyl tert-butyl ether and the supernatant was decanted off. The residue was then stirred with 150 ml of dichloromethane, the product crystallizing out. The 3(R,S)-bromo-1-methyl-4-(2,4,6-trimethoxyphenyl)-1,2,3,6-tetrahydropyridine hydrobromide (VI) obtained was filtered off with suction, washed with 50 ml of dichloromethane and dried in vacuo.

Yield: 147 g of almost colorless crystals.
M.p.: 190–192° C.;
$MS(ES^+)$: 342.2$(M+H)^+$.

Example 2

Preparation of 3(R,S)-Hydroxy-1-methyl-4-(2,4,6-trimethoxyphenyl)-1,2,3,6-tetrahydropyridine (VII)

50 g (0.118 mol of 3(R,S)-bromo-1-methyl-4-(2,4,6-trimethoxyphenyl)-1,2,3,6-tetrahydropyridine hydrobromide (VI) were heated under reflux for 2 h in 100 ml of water. The reaction mixture was then cooled to 20° C. and adjusted to pH 12.5 by dropwise addition of 30 ml of 30% strength sodium hydroxide solution. After a short time, a pale brown precipitate crystallized out. The mixture was stirred at 5–10° C. for a further 1 h, and the precipitated product was filtered off with suction and washed with 30 ml of water. The crude product was then stirred with 20 ml of acetone, filtered off with suction and dried in vacuo.

Yield: 25.2 g of colorless crystals;
M.p.: 125–127° C.;
$MS(CI^+)$: 280.3$(M+H)^+$.

Example 3

Preparation of 3(R,S)-Hydroxy-1-methyl-4-(2,4,6-trimethoxyphenyl)-1,2,3,6-tetrahydropyridine (VII)

75.7 ml (0.44 mol) of 33% strength HBr in glacial acetic acid were added to 100 ml of glacial acetic acid and 50 g (0.44 mol) of 1-methylpiperidin-4-one (III) were then vigorously added dropwise at 20–25 ° C. with ice-cooling. 70.4 g (0.44 mol) of bromine were added dropwise at 20–25° C. under nitrogen in the course of 30 min to the suspension of the hydrobromide obtained in this way, a clear, yellowish solution being obtained. This was stirred at 25° C. for a further 60 min and 67.2 g (0.40 mol) of 1,3,5-trimethoxybenzene (V) were then added to the reaction solution. It was then stirred at 25° C. for 1 h. After this, 400 ml of water were allowed to run in and the mixture was heated to reflux for 3 h. The reaction mixture was allowed to stand at room temperature overnight, diluted with 400 ml of water and then cooled to 10° C., and a total of 320 ml of conc. sodium hydroxide solution were added dropwise at this temperature in the course of 4 h to the well stirred mixture (pH after addition 10.7). In the course of this the allyl alcohol (VII) first precipitated in slightly oily form, but then on longer stirring became solid and could readily be filtered off with suction. The dark yellow precipitate was filtered off with suction, washed with water and dried well. The crude product was then stirred with 80 ml of acetone, filtered off with suction and dried in vacuo.

Yield: 55 g of pale yellow crystals;
M.p.: 125–127° C.;
$MS(CI^+)$: 280.3$(M+H)^+$;
$^1$H-NMR(dmso-$d_6$): δ (ppm)6.15(s, 2H); 5.65(dd, 1H); 4.20(m, 1H); 3.80(s, 3H); 3.75(s, 6H); 3.31(dd1H); 2.89(m, 1H); 2.84(dd, 1H); 2.71(d, 1H); 2.57(dd, 1H); 2.24(s, 3H).

Example 4

Preparation of 3(R,S)-Hydroxy-1-methyl-4-(2,4,6-trimethoxyphenyl)-1,2,3,6-tetrahydropyridine (VII)

75.7 ml (0.44 mol) of 33% strength HBr in glacial acetic acid were added to 100 ml of glacial acetic acid and 50 g (0.44 mol) of 1-methylpiperidin-4-one (III) were then rapidly added dropwise at 20–25° C. with ice cooling. 70.4 g (0.44 mol) of bromine were added dropwise at 20–25° C. under nitrogen in the course of 30 min to the suspension of the hydrobromide obtained in this way, a clear, yellowish solution being obtained. This was stirred at 25° C. for 60 min and 67.2 g (0.40 mol) of 1,3,5-trimethoxybenzene (V) were then added to the reaction solution. After 15 min, a further 40.8 g (0.4 mol) of acetic anhydride were added with cooling and the mixture was stirred at 25° C. for 1 h. After this, 750 ml of water were allowed to run in and the mixture was heated at 80° C. for 9.5 h. The reaction mixture was then cooled to 5–10° C. and adjusted to pH 5.5 by dropwise addition of 200 ml of conc. sodium hydroxide solution in the course of 30 min. In the course of this, unreacted 1,3,5-trimethoxybenzene precipitated. The suspension was filtered and the filtrate was adjusted to pH 14 at 5–10° C. using a further 200 ml of conc. sodium hydroxide solution. In the course of this, the allyl alcohol (VII) initially precipitated in slightly oily form, but on longer stirring became solid and could then be readily filtered off with suction. The batch stood overnight at room temperature. The pale yellow precipitate was then filtered off with suction, washed with 300 ml of water to neutral pH and dried well. Crude yield: 87.2 g of pale yellow crystals. The crude product was then stirred with 100 ml of acetone, filtered off with suction and dried in vacuo.

Yield: 73 g of pale yellow crystals;
M.p.: 125–127° C.;
$MS(CI^+)$: 280.3$(M+H)^+$.

Example 5

Preparation of Racemic 3,4-cis Alcohol (VIII)

3.5 g (12.5 mmol) of 3(R,S)-hydroxy-1-methyl-4-(2,4,6-trimethoxyphenyl)-1,2,3,6-tetrahydropyridine (VII) were dissolved in 100 ml of methanol and treated with 0.35 g of catalyst (5% Pd/C, previously washed with MeOH) and hydrogenated in a Büchi autoclave for 15 h at 50° C. and a hydrogen pressure of 50 bar. The catalyst was then filtered off, the filtrate was evaporated in vacuo on a rotary evaporator and the residue was stirred with 4 ml of acetone. The product obtained was filtered off and dried in vacuo.

Yield: 2.7 g of colorless crystals;
M.p.: 131–132° C.;
$MS(CI^+)$: 282.3$(M+H)^+$.

Example 6

Preparation of Racemic 3,4-cis Alcohol (VIII)

10.0 g (35.8 mmol) of 3(R,S)-hydroxy-1-methyl-4-(2,4,6-trimethoxyphenyl)-1,2,3,6-tetrahydropyridine (VII) were dissolved in 100 ml of methanol and treated with 1.5 g of catalyst (5% Pd/C, previously washed with MeOH) and hydrogenated in a Büchi autoclave for 39 h at 50° C. and a hydrogen pressure of 50 bar. The catalyst was then filtered off, the filtrate was evaporated in vacuo on a rotary evaporator and the residue was stirred with 20 ml of acetone. The product obtained was filtered off and dried in vacuo.

Yield: 9.2 g of colorless crystals;
M.p.: 131–132° C.;
MS(Cl⁺): 282.3(M+H)⁺.

Example 7

Preparation of 3(R,S)-Acetoxy-1-methyl-4-(2,4,6-trimethoxyphenyl)-1,2,3,6-tetrahydropyridine (IXa) [R=methyl]

2.79 g (10 mmol) of 3(R,S)-hydroxy-1-methyl-4-(2,4,6-trimethoxyphenyl)-1,2,3,6-tetrahydropyridine (VII) were dissolved in 15 ml of acetic anhydride and stirred at 100° C. for 4 h. The solution was then evaporated in vacuo in a rotary evaporator and the residue was dissolved in 10 ml of water, adjusted to pH>12 with sodium hydroxide solution and extracted twice with 20 ml of ethyl acetate each time. The combined organic phases were washed with 10 ml of saturated sodium chloride solution, then dried over sodium sulfate and evaporated in vacuo on a rotary evaporator.

Yield: 2.55 g of an oil;
MS(ES⁺): 322.2(M+H)⁺.

Example 8

Preparation of 3(R,S)-Methyloxycarbonyloxy-1-methyl-4-(2,4,6-trimethoxyphenyl)-1,2,3,6-tetrahydropyridine (IXb) [R=methyl]

8.37 g (30 mmol) of 3(R,S)-hydroxy-1-methyl-4(2,4,6-trimethoxyphenyl)-1,2,3,6-tetrahydropyridine (VII) were dissolved in 83.7 ml of tetrahydrofuran and treated with 12.4 ml (90 mmol) of triethylamine. The mixture was cooled to 5° C., 2.55 ml (33 mmol) of methyl chloroformate were added dropwise in the course of 15 min and the mixture was stirred at 5–10° C. for a further 3 h. Since TLC checking still showed starting material, a further 1.0 ml (12.9 mmol) of methyl chloroformate were added and the mixture was stirred again for 1 h. 50 ml of water were then added and the mixture was extracted twice with 50 ml of ethyl acetate each time. The combined organic phases were washed with 30 ml of saturated sodium chloride solution, then dried over sodium sulfate and evaporated in vacuo on a rotary evaporator.

Yield: 8.7 g of an oil which becomes solid on allowing to stand;
MS(ES⁺): 338.2(M+H)⁺.

Example 9

Preparation of Racemic cis Ester (Xa) [R=methyl]

15.33 g of toluenesulfonic acid salt of 3(R,S)-acetoxy-1-methyl-4-(2,4,6-trimethoxyphenyl)-1,2,3,6-tetrahydropyridine (IXa) [R=methyl] were dissolved in 153 ml of methanol, filtered through active carbon and the filtrate was treated with 1.53 g of catalyst (5% Rh/C) and hydrogenated in a Büchi autoclave for 24 h at 50° C. and a hydrogen pressure of 18 bar. The catalyst was then filtered off and the filtrate was evaporated in vacuo on a rotary evaporator. The residue was dissolved in 50 ml of water and adjusted to a pH of >12 using conc. sodium hydroxide solution. After a short time, the base precipitated. The product obtained was filtered off, washed with water and dried in vacuo.

Yield: 8.5 g of colorless crystals;
M.p.: 115–117° C.;
MS(Cl⁺): 324.2(M+H)⁺.

Example 10

Preparation of Racemic 3,4-cis Alcohol (VIII) from (Xa) [R=methyl]

1.61 g (5 mmol) of racemic cis ester (Xa) [R =methyl] were heated under reflux for 8 h in 20 ml of methanol and with 5 ml of conc. hydrochloric acid. The methanol was then removed in vacuo, the residue was treated with 10 ml of water and a pH of >12 was set using conc. sodium hydroxide solution. In the course of this the product precipitated. The product obtained was filtered off, washed with water and dried in vacuo.

Yield: 1.1 g of colorless crystals;

M.p.: 131–132° C.;

MS(Cl⁺): 282.4(M+H)⁺.

What is claimed is:

1. A process for preparing (−)cis-3-hydroxy-1-methyl-4-(2,4,6-trimethoxyphenyl)piperidine (II)

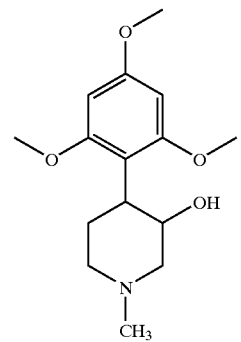

(II)

comprising either resolving (3,4-cis)-3-(R,S)-hydroxy-1-methyl-4-(2,4,6-trimethoxyphenyl)piperidine (VIII)

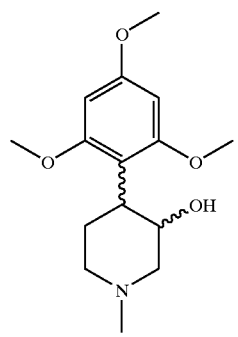

VIII to obtain the (−)cis-3-hydroxy-1-methyl-4-(2,4,6-trimethoxyphenyl)piperidine (II) in substantial enantiomeric purity;

or resolving at least one compound (Xa) or at least one compound (Xb)

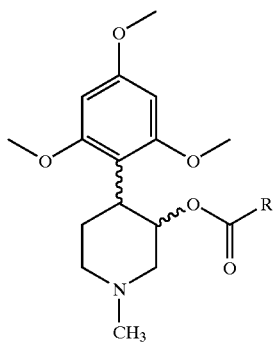

Xa

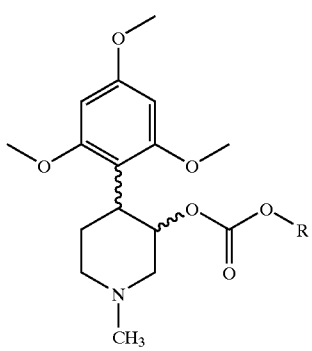

Xb wherein R is chosen from $(C_1-C_{16})$-alkyl, $(C_6-C_{14})$-aryl-$(C_1-C_{16})$-alkyl, and $(C_6-C_{14})$-aryl, and in the at least one compound (Xa), R is also optionally carboxy-$(C_2-C_6)$-alkyl, to form at least one resolved compound (Xa) or at least one resolved compound (Xb), and converting the at least one resolved compound (Xa) or the at least one resolved compound (Xb) into the (−)cis-3-hydroxy-1-methyl-4-(2,4,6-trimethoxyphenyl) piperidine (II) in substantial enantiomeric purity;

or resolving at least one ester (IXa) or at least one carbonate (IXb)

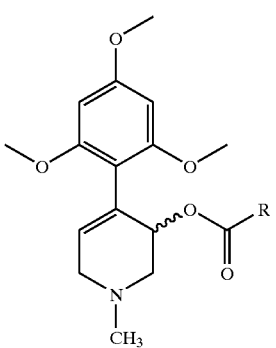

IXa

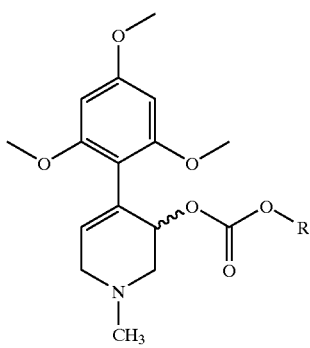

IXb in which R is chosen from $(C_1-C_{16})$-alkyl, $(C_6-C_{14})$-aryl-$(C_1-C_{16})$-alkyl, or $(C_6-C_{14})$-aryl, and in the at least one ester (IXa) R is also optionally carboxy-$(C_2-C_6)$-alkyl, into a resolved product, and hydrogenating the resolved product to obtain the (−)cis-3-hydroxy-1-methyl-4-(2,4,6-trimethoxyphenyl) piperidine (II) in substantial enantiomeric purity;

or resolving isolated 3(R,S)-hydroxy-1-methyl-4-(2,4,6-trimethoxyphenyl)-1,2,3,6-tetrahydropyridine (VII)

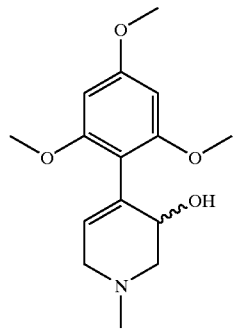

VII to obtain a resolved isolated product, and hydrogenating the resolved isolated product to obtain the (−)cis-3-hydroxy-1-methyl-4-(2,4,6-trimethoxyphenyl)piperidine (II) in substantial enantiomeric purity.

2. The process as claimed in claim 1, wherein resolving (3,4-cis)-3-(R,S)-hydroxy-1-methyl-4-(2,4,6-trimethoxyphenyl)-piperidine (VIII) is performed with at least one suitable chiral auxiliary reagent.

3. The process of claim 1, wherein (3,4-cis)-3-(R,S)-hydroxy-1-methyl-4-(2,4,6-trimethoxyphenyl)-piperidine (VIII) is obtained by hydrogenating isolated 3(R,S)-hydroxy-1-methyl-4-(2,4,6-trimethoxyphenyl)-1,2,3,6-tetrahydropyridine (VII)

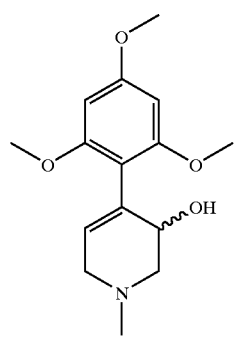

VII to yield the (3,4-cis)-3-(R,S)-hydroxy-1-methyl-4-(2,4,6-trimethoxyphenyl)-piperidine (VIII);

or reacting isolated 3(R,S)-hydroxy-1-methyl-4-(2,4,6-trimethoxyphenyl)-1,2,3,6-tetrahydropyridine (VII) to form at least one ester (IXa) or to form at least one carbonate (IXb),

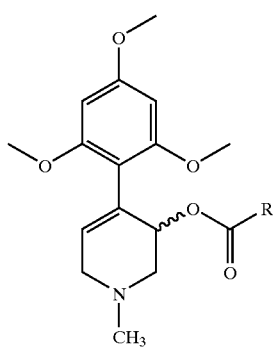

IXa

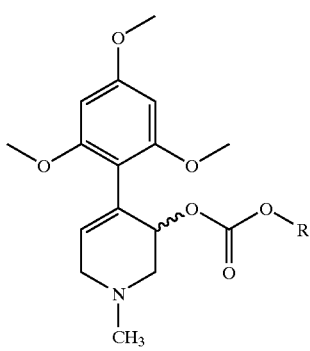

IXb in which R is chosen from $(C_1-C_{16})$-alkyl, $(C_6-C_{14})$-aryl-$(C_1-C_{16})$-alkyl, or $(C_6-C_{14})$-aryl, and in the at least one ester (IXa) R is also optionally carboxy-$(C_2-C_6)$-alkyl, and hydrogenating the at least one ester (IXa) to give at least one compound (Xa), or hydrogenating the at least one carbonate (IXb) to give at least one compound (Xb),

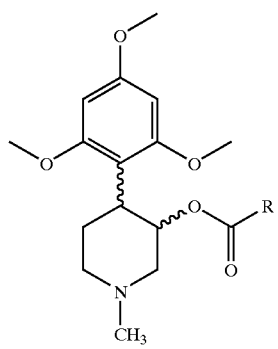

Xa

Xb wherein R is chosen from $(C_1-C_{16})$-alkyl, $(C_6-C_{14})$-aryl-$(C_1-C_{16})$-alkyl, and $(C_6-C_{14})$-aryl, and in the at least one compound (Xa), R is also optionally carboxy-$(C_2-C_6)$-alkyl, and liberating the (3,4-cis)-3-(R,S)-hydroxy-1-methyl-4-(2,4,6-trimethoxyphenyl)-piperidine (VIII) from the at least one compound (Xa) or from the at least one compound (Xb).

4. The process as claimed in claim 3, wherein the hydrogenating is catalytic hydrogenating performed in one or more suitable solvents.

5. The process as claimed in claim 3, wherein (3,4-trans)-3-(R,S)-hydroxy-1-methyl-4-(2,4,6-trimethoxyphenyl)-piperidine is separated from the (3,4-cis)-3-(R,S)-hydroxy-1-methyl-4-(2,4,6-trimethoxyphenyl)-piperidine (VIII) by crystallizing from one or more suitable solvents.

6. The process as claimed in claim 1, wherein the at least one compound (Xa) or the at least one compound (Xb) is obtained by reacting isolated 3(R,S)-hydroxy-1-methyl-4-(2,4,6-trimethoxyphenyl)-1,2,3,6-tetrahydropyridine (VII)

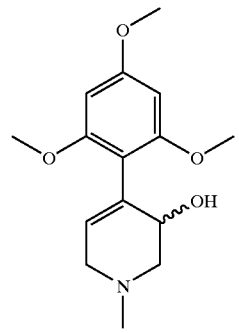

VII to form at least one ester (IXa) or to form at least one carbonate (IXb)

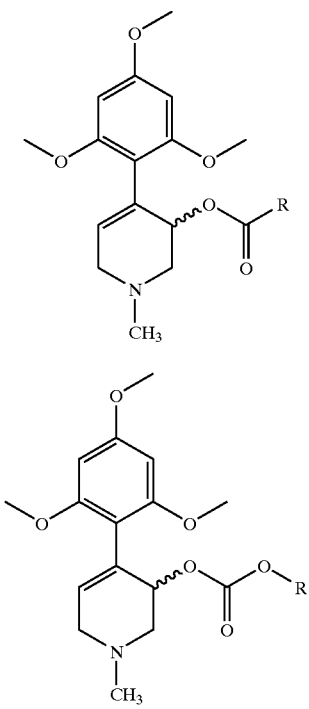

in which R is chosen from $(C_1–C_{16})$-alkyl, $(C_6–C_{14})$-aryl-$(C_1–C_{16})$-alkyl, or $(C_6–C_{14})$-aryl, and in the at least one ester (IXa) R is also optionally carboxy-$(C_2–C_6)$-alkyl, and hydrogenating the at least one ester (IXa) to give the at least one compound (Xa), or hydrogenating the at least one carbonate (IXb) to give at the least one compound (Xb).

7. The process as claimed in claim 6, wherein the hydrogenating is catalytic hydrogenating.

8. The process as claimed in claim 1, wherein the at least one ester (IXa) or the at least one carbonate (IXb) is obtained by reacting isolated 3(R,S)-hydroxy-1-methyl-4-(2,4,6-trimethoxyphenyl)-1,2,3,6-tetrahydropyridine (VII)

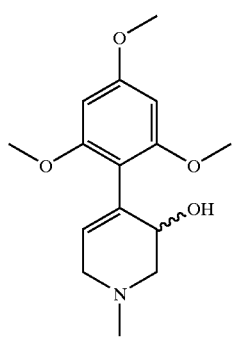

to form the at least one ester (IXa) or to form the at least one carbonate (IXb).

9. The process as claimed in claim 1, 3, 6, or 8, wherein the isolated 3(R,S)-hydroxy-1-methyl-4-(2,4,6-trimethoxyphenyl)-1,2,3,6-tetrahydropyridine (VII) is obtained by bringing a first reaction solution to a temperature ranging from about 0° C. to about 30° C., wherein the first reaction solution has a pH and comprises crude 3(R,S)-hydroxy-1-methyl-4-(2,4,6-trimethoxyphenyl)-1,2,3,6-tetrahydropyridine (VII),

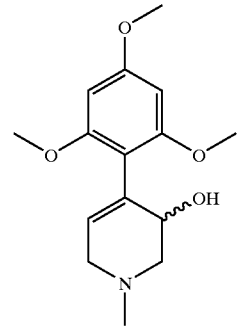

optionally diluting the first reaction solution with water, adjusting the pH of the first reaction solution to a pH of about 12 or greater at a temperature ranging from about 0° C. to about 30° C., causing 3-(R,S)-hydroxy-1-methyl-4-(2,4,6-trimethoxyphenyl)-1,2,3,6-tetrahydropyridine (VII) to form a first precipitate, filtering off the first precipitate with suction, optionally purifying the first precipitate by dissolving the first precipitate in a second reaction solution having a pH, filtering, optionally extracting the second reaction solution with at least one water immiscible solvent or a mixture thereof to form an aqueous phase having a pH, adjusting the pH of the second reaction solution or the pH of the aqueous phase to a pH of about 12 or greater, causing 3(R,S)-hydroxy-1-methyl-4-(2,4,6-trimethoxyphenyl)-1,2,3,6-tetrahydropyridine (VII) to form a second precipitate, optionally extracting the second precipitate by stirring with one or more suitable organic solvents or a mixture thereof, yielding the isolated 3-(R,S)-hydroxy-1-methyl-4-(2,4,6-trimethoxyphenyl)-1,2,3,6-tetrahydropyridine (VII) in the first precipitate or the second precipitate.

10. The process as claimed in claim 9, wherein the adjusting of pH to a pH of about 12 or greater is performed by adding aqueous alkali.

11. The process as claimed in claim 9, wherein the second reaction solution comprises aqueous hydrochloric acid.

12. The process of claim 9, wherein the crude 3-(R,S)-hydroxy-1-methyl-4-(2,4,6-trimethoxyphenyl)-1,2,3,6-tetrahydropyridine (VII) is obtained by either reacting solid 3(R,S)-bromo-1-methyl-4-(2,4,6-trimethoxyphenyl)-1,2,3,6-tetrahydropyridine hydrobromide (VI)

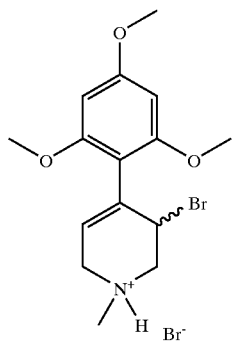

VI with water, to give the crude 3(R,S)-hydroxy-1-methyl-4-(2,4,6-trimethoxyphenyl)-1,2,3,6-tetrahydropyridine (VII), or treating a third reaction solution comprising 3(R,S)-bromo-1-methyl-4-(2,4,6-trimethoxyphenyl)-1,2,3,6-tetrahydropyridine hydrobromide (VI)

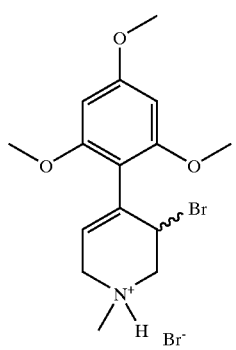

VI with water and reacting by stirring at a temperature ranging from about 50° C. to about 100° C. to give the crude 3(R,S)-hydroxy-1-methyl-4-(2,4,6-trimethoxyphenyl)-1,2,3,6-tetrahydropyridine (VII).

13. The process as claimed in claim 12, wherein either of the reacting is performed with stirring.

14. The process as claimed in claim 12, wherein either of the reacting occurs at a temperature ranging from about 50° C. to about 100° C.

15. The process as claimed in claim 14, wherein the temperature ranges from about 60° C. to about 80° C.

16. The process as claimed in claim 12, wherein the 3(R,S)-bromo-1-methyl-4-(2,4,6-trimethoxyphenyl)-1,2,3,6-tetrahydropyridine hydrobromide (VI) is obtained by adding an amount of 1,3,5-trimethoxybenzene (V)

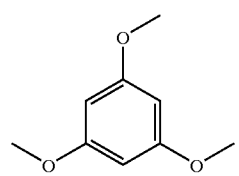

V to a fourth reaction solution, wherein the fourth reaction solution comprises 3(R,S)-bromo-1-methyl-4-oxopiperidine hydrobromide (IV)

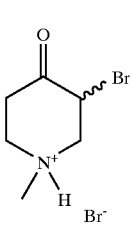

IV and reacting to give the third reaction solution comprising the 3(R,S)-bromo-1-methyl-4-(2,4,6-trimethoxyphenyl)-1,2,3,6-tetrahydropyridine hydrobromide (VI),

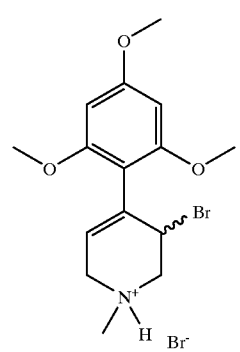

VI optionally adding acetic anhydride to the third reaction solution in an amount sufficient to remove some or substantially all of any water of reaction formed, optionally isolating the solid 3(R,S)-bromo-1-methyl-4-(2,4,6-trimethoxyphenyl)-1,2,3,6-tetrahydropyridine hydrobromide (VI) by stirring the third reaction solution into a suitable organic solvent.

17. The process as claimed in claim 16, wherein the amount of 1,3,5-trimethoxybenzene (V) added ranges from about 0.8 to about 1 equivalent.

18. The process as claimed in claim 16, wherein the reacting is performed at a temperature ranging from about 0° C. to about 30° C.

19. The process as claimed in claim 16, wherein the 3(R,S)-bromo-1-methyl-4-oxopiperidine hydrobromide (IV) is obtained by reacting 1-methylpiperidin-4-one hydrobromide with bromine to give the 3(R,S)-bromo-1-methyl-4-oxopiperidine hydrobromide (IV).

20. The process as claimed in claim 19, wherein the 1-methylpiperidin-4-one hydrobromide is obtained by converting 1-methylpiperidin-4-one (III)

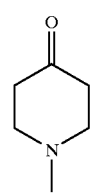

III into the 1-methylpiperidin-4-one hydrobromide.

21. The process as claimed in claim 20, wherein the converting comprises introducing 1-methylpiperidin-4-one (III) into a fifth reaction solution comprising HBr and glacial acetic acid to produce the 1-methylpiperidin-4-one hydrobromide.

22. A process for preparing 3-(R,S)-hydroxy-1-methyl-4-(2,4,6-trimethoxyphenyhl)-1,2,3,6-tetrahydropyridine (VII)

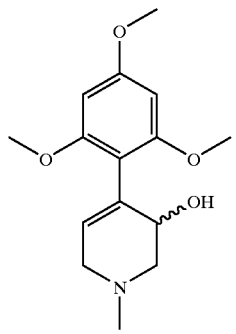

VII the process comprising
reacting 3(R,S)-bromo-1-methyl-4-(2,4,6-trimethoxyphenyl)-1,2,3,6-tetrahydropyridine hydrobromide (VI)

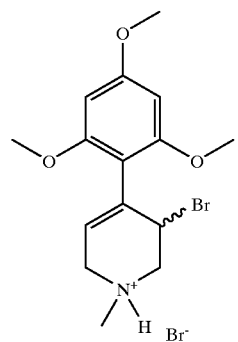

VI with water, to give the 3(R,S)-hydroxy-1-methyl-4-(2,4,6-trimethoxyphenyl)-1,2,3,6-tetrahydropyridine (VII).

23. The process as claimed in claim 22, wherein the reacting is performed with stirring.

24. The process as claimed in claim 22, wherein the reacting occurs at a temperature ranging from about 50° C. to about 100° C.

25. The process as claimed in claim 24, wherein the temperature ranges from about 60° C. to about 80° C.

26. The process as claimed in claim 22, wherein the 3(R,S)-bromo-1-methyl-4-(2,4,6-trimethoxyphenyl)-1,2,3,6-tetrahydropyridine hydrobromide (VI) is obtained by
combining an amount of 1,3,5-trimethoxybenzene (V)

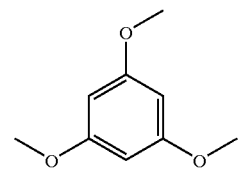

V with an amount of 3(R,S)-bromo-1-methyl-4-oxopiperidine hydrobromide (IV)

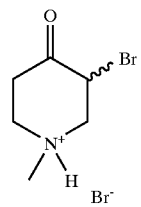

IV and reacting to give the 3(R,S)-bromo-1-methyl-4-(2,4,6-trimethoxyphenyl)-1,2,3,6-tetrahydropyridine hydrobromide (VI).

27. The process as claimed in claim 26, wherein the amount of 1,3,5-trimethoxybenzene (V) added ranges from about 0.8 to about 1 equivalent.

28. The process as claimed in claim 26, wherein the reacting is performed at a temperature ranging from about 0° C. to about 30° C.

29. A process for preparing 3(R,S)-bromo-1-methyl-4-oxopiperidine hydrobromide (IV)

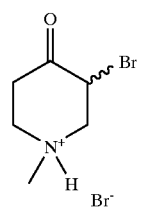

IV the process comprising
reacting 1-methylpiperidin-4-one hydrobromide with bromine to give the 3(R,S)-bromo-1-methyl-4-oxopiperidine hydrobromide (IV).

30. The process as claimed in claim 29, wherein the 1-methylpiperidin-4-one hydrobromide is obtained by
converting 1-methylpiperidin-4-one (III)

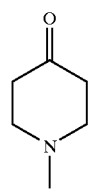

III into the 1-methylpiperidin-4-one hydrobromide.

31. The process as claimed in claim 30, wherein the converting comprises introducing 1-methylpiperidin-4-one (III) into an sixth reaction solution comprising HBr and glacial acetic acid to produce the 1-methylpiperidin-4-one hydrobromide.

* * * * *

UNITED STATES PATENT AND TRADEMARK OFFICE
CERTIFICATE OF CORRECTION

PATENT NO. : 6,437,136 B2
DATED : August 20, 2002
INVENTOR(S) : Breipohl et al.

It is certified that error appears in the above-identified patent and that said Letters Patent is hereby corrected as shown below:

Column 15,
Line 38, "at the least" should read -- the at least --.

Column 19,
Line 2, "trimethoxyphenyhl" should read -- trimethoxyphenyl --.

Column 20,
Line 58, "an sixth" should read -- a sixth --.

Signed and Sealed this

Third Day of December, 2002

JAMES E. ROGAN
*Director of the United States Patent and Trademark Office*